United States Patent
Coombs et al.

(10) Patent No.: US 11,946,371 B2
(45) Date of Patent: Apr. 2, 2024

(54) NON-DESTRUCTIVE TESTING DEVICE CUSTOMIZATION

(71) Applicant: Baker Hughes Oilfield Operations LLC, Houston, TX (US)

(72) Inventors: Kevin A. Coombs, Skaneateles, NY (US); Matthew W. Pankow, Camillus, NY (US)

(73) Assignee: Baker Hughes Oilfield Operations LLC, Houston, TX (US)

( * ) Notice: Subject to any disclaimer, the term of this patent is extended or adjusted under 35 U.S.C. 154(b) by 430 days.

(21) Appl. No.: 17/307,702

(22) Filed: May 4, 2021

(65) Prior Publication Data
US 2021/0363827 A1 Nov. 25, 2021

Related U.S. Application Data

(60) Provisional application No. 63/028,923, filed on May 22, 2020.

(51) Int. Cl.
| | | |
|---|---|---|
| E21B 6/06 | (2006.01) | |
| E21B 37/00 | (2006.01) | |
| E21B 47/12 | (2012.01) | |

(52) U.S. Cl.
CPC ............... *E21B 6/06* (2013.01); *E21B 37/00* (2013.01); *E21B 47/12* (2013.01)

(58) Field of Classification Search
CPC ............ E21B 6/06; E21B 37/00; E21B 47/12; G01N 21/954; G01M 5/0033; G01M 5/0075
See application file for complete search history.

(56) References Cited

U.S. PATENT DOCUMENTS

| 4,837,714 A | 6/1989 | Brookner et al. |
| 6,327,921 B1 | 12/2001 | Hsu et al. |

(Continued)

FOREIGN PATENT DOCUMENTS

| CN | 108287193 A | 7/2018 |
| KR | 20140059012 A | 5/2014 |

(Continued)

OTHER PUBLICATIONS

Gul, S. et al., "Smartphone controlled ultrasonic nondestructive testing system design," International Conference on Engineering Technologies (ICENTE'17), Dec. 7-9, 2017, 5 pages.

(Continued)

*Primary Examiner* — Francis C Gray
(74) *Attorney, Agent, or Firm* — Mintz, Levin, Cohn, Ferris, Glovsky and Popeo, P.C.

(57) ABSTRACT

A method for customizing non-destructive testing is provided and includes receiving, by a non-destructive testing (NDT) device, a stock application. The method further includes the device performing a stock NDT function in response to execution of the stock application. The stock NDT function can include a first device manipulation, a first NDT data acquisition by a device sensor, a first analysis employing data acquired by the first NDT data acquisition, or a first NDT output. The method additionally includes the device receiving a custom application after receipt of the stock application. The method also includes the device performing a custom NDT function, different from the stock NDT functions, and including at least one of a second device manipulation, a second NDT data acquisition by a sensor of the device, a second analysis employing data acquired by the second NDT data acquisition, or a second NDT output.

16 Claims, 4 Drawing Sheets

(56) References Cited

U.S. PATENT DOCUMENTS

| | | | |
|---|---|---|---|
| 9,489,124 B2* | 11/2016 | Schiefer | G06F 3/0488 |
| 10,484,438 B2 | 11/2019 | Soorianarayanan et al. | |
| 2012/0074305 A1* | 3/2012 | Scholes | G01V 5/0025 |
| | | | 250/271 |
| 2014/0188423 A1* | 7/2014 | Messinger | G01B 15/00 |
| | | | 702/108 |
| 2014/0189851 A1* | 7/2014 | Domke | G06F 21/41 |
| | | | 726/17 |
| 2014/0268541 A1* | 9/2014 | Coombs | A61B 1/00066 |
| | | | 361/679.41 |
| 2015/0350639 A1* | 12/2015 | Maule | G06F 3/0481 |
| | | | 348/187 |
| 2019/0033571 A1 | 1/2019 | Maule et al. | |

FOREIGN PATENT DOCUMENTS

| | | |
|---|---|---|
| KR | 20150096184 A | 8/2015 |
| WO | 2019-204408 A1 | 10/2019 |

OTHER PUBLICATIONS

Popovici, Marius; "Nondestructive Investigation Methods for Mechanical Equipment: Thermal & Ultrasound," Fiabilitate si Durabilitate—Fiability & Durability, Supplement No. Jan. 2013, pp. 228-233.

International Search Report and Written Opinion for International Application No. PCT/US2021/031581, dated Sep. 1, 2021.

* cited by examiner

NON-DESTRUCTIVE TESTING DEVICE CUSTOMIZATION

CROSS-REFERENCE TO RELATED APPLICATIONS

This application claims the benefit of U.S. Provisional Patent Application No. 63/028,923, filed on May 22, 2020 and entitled "Non-Destructive Testing Device Customization," the entirety of which is incorporated by reference.

BACKGROUND

Certain equipment and facilities, such as power generation equipment and facilities, oil and gas equipment and facilities, aircraft equipment and facilities, manufacturing equipment and facilities, and the like, include interrelated systems and processes. For example, power generation plants can include turbine systems and processes for operating and maintaining the turbine systems. Likewise, oil and gas operations can include carbonaceous fuel retrieval systems and processing equipment interconnected via pipelines. Similarly, aircraft systems can include airplanes and maintenance hangars useful in maintaining airworthiness and providing for maintenance support. During equipment operations, the equipment can degrade, encounter undesired conditions such as corrosion, wear and tear, etc., potentially affecting overall equipment effectiveness. Certain inspection techniques, such as non-destructive inspection techniques or non-destructive testing (NDT) techniques, can be used to detect undesired equipment conditions.

SUMMARY

Certain NDT devices can be used to observe the inner mechanisms of complex machines, such as turbines and oil and gas equipment. As an example, NDT devices such as borescopes endoscopes, etc. can be fed through these complex machines to perform maintenance checks without dismantling the whole machine. Such NDT devices can be actuated (e.g., translated, rotated, bent, etc.) in order to maneuver through small openings of these complex machines to allow inspection of these inner components. Acquired NDT inspection data, analysis of the acquired NDT inspection data, storage and/or display of the acquired and analyzed NDT inspection data can be performed by the NDT device, display another computing device, or combinations thereof.

The functionality of existing NDT devices are generally implemented by software (e.g., applications) and feature sets that are provided by the manufacturer. However, the ability to customize the "stock" functionality implemented by manufacturer-provided applications can be limited or even prohibited. Thus, end users may lack the ability to customize the functionality of NDT devices to best suit their desired procedures and applications.

Accordingly, embodiments of the present disclosure provide systems and methods to facilitate customization of the functions of NDT equipment. As an example, one or more tools (e.g., software development kits (SDKs), application programming interfaces (APIs), toolkits, etc.) can be provided to allow NDT device owners and third parties to develop applications (e.g., plug-ins) that have programmatic access to NDT specific functionality of NDT devices. Such applications, when executed, can provide extended functionality for NDT devices, such as configuration, movement, data acquisition, data analysis, data output, and the like. Such extended functionality can be different from, and can operate in addition to or in lieu of, the functionality provided by "stock" manufacturer-provided applications. As an example, some applications can be configured to completely take over the user experience, while others can operate in the background or as an extension might (e.g., in a user interface frame or pop-up).

In an embodiment, a method for customizing non-destructive testing is provided. The method can include receiving, by a non-destructive testing (NDT) device, a stock application. The method can further include performing, by the NDT device, one or more stock NDT functions in response to execution of the stock application. The one or more stock NDT functions can also include at least one of a first manipulation of the NDT device, a first NDT data acquisition by a sensor of the NDT device, a first analysis employing data obtained by the first NDT data acquisition or a first NDT output. The method can additionally include receiving, by the NDT device, one or more customized NDT-specific applications after receipt of the one or more stock applications. The method can also include performing, by the NDT device, one or more custom NDT functions in response to execution of a customized NDT-specific application, the one or custom NDT functions being different from stock NDT functions and including at least one of a second manipulation of the NDT device, a second NDT data acquisition by a sensor of the NDT device, a second analysis of the first NDT, or a second NDT output.

In an embodiment, the NDT device can be a borescope.

In an embodiment, the first and second manipulations can be different articulations of a tip of the borescope.

In an embodiment, the second manipulation can be at least one of a translation or rotation of a probe driver of the borescope.

In an embodiment, the one or more custom NDT functions can include input of one or more configuration settings of the sensor that performs the second NDT data acquisition.

In an embodiment, the second manipulation can be movement of the target with respect to the NDT device performed by a turning tool coupled to the target.

In an embodiment, the custom NDT functions can further include control of an illumination of the target.

In an embodiment, a non-transitory computer-readable medium is provided. The non-transitory computer-readable medium includes instructions that, when executed, can be configured to cause an NDT device to receive one or more stock applications. The instructions can be further configured to cause the NDT device to perform one or more stock NDT functions in response to execution of the stock application. The one or more stock NDT functions can include at least one of a first manipulation of the NDT device, a first NDT data acquisition by a sensor of the NDT device, a first analysis employing data acquired by the first NDT data acquisition, or a first NDT output. The instructions can also be configured to cause the NDT device to receive one or more customized NDT-specific applications after receipt of the one or more stock applications. The instructions can further be configured to cause the NDT device to perform one or more custom NDT functions in response to execution of the customized NDT-specific application. The one or custom NDT functions can be different from the stock NDT functions and can include at least one of a second manipulation of the NDT device, a second NDT data acquisition by a sensor of the NDT device, a second analysis employing data obtained by the second NDT data acquisition, or a second NDT output.

In another embodiment, the NDT device can be a borescope.

In another embodiment, the first and second manipulation can be different articulations of a tip of the borescope.

In another embodiment, the second manipulation can be at least one of a translation or rotation of a probe driver of the borescope.

In another embodiment, the one or more custom NDT functions can include input of one or more configuration settings of the sensor that performs the second NDT data acquisition.

In another embodiment, the second manipulation can be movement of the target with respect to the NDT device performed by a turning tool coupled to the target.

In another embodiment, the custom NDT functions can further include control of an illumination of the target.

DESCRIPTION OF DRAWINGS

These and other features will be more readily understood from the following detailed description taken in conjunction with the accompanying drawings, in which.

It is noted that the drawings are not necessarily to scale. The drawings are intended to depict only typical aspects of the subject matter disclosed herein, and therefore should not be considered as limiting the scope of the disclosure.

DETAILED DESCRIPTION

Non-destructive testing (NDT) devices are commonly employed to inspect equipment and facilities, such as power generation equipment and facilities, oil and gas equipment and facilities, aircraft equipment and facilities, manufacturing equipment and facilities, and the like. NDT devices can include stock applications prepared by the NDT device manufacturer that when executed, provide for manipulation of the NDT device, acquisition of data by the NDT device, analysis of data acquired by the NDT device, graphical user interfaces, display of acquired and analyzed data, etc. However, given the wide variety of NDT devices, prospective equipment to be inspected, and possible analyses of data acquired during NDT inspection, it can be difficult for stock applications to cover every possible use case. Furthermore, customers can desire to maintain certain NDT testing procedures and/or analyses proprietary and private. Accordingly, systems and methods are provided for customizing the above-discussed functionality of NDT devices, such as borescopes. As an example, customized NDT-specific applications can be installed on top of existing stock applications and allow the functions of the NDT device to be changed or superseded. Beneficially, such changes can significantly improve the ease of NDT inspection, increase throughput of NDT testing, and/or reduce NDT inspection cost.

Embodiments of sensing systems and corresponding methods for customizing the functionality of NDT devices are discussed herein with specific reference to borescopes. However, it can be understood that embodiments of the disclosure can be employed for customizing the functionality of any NDT device without limit.

Figure 1:
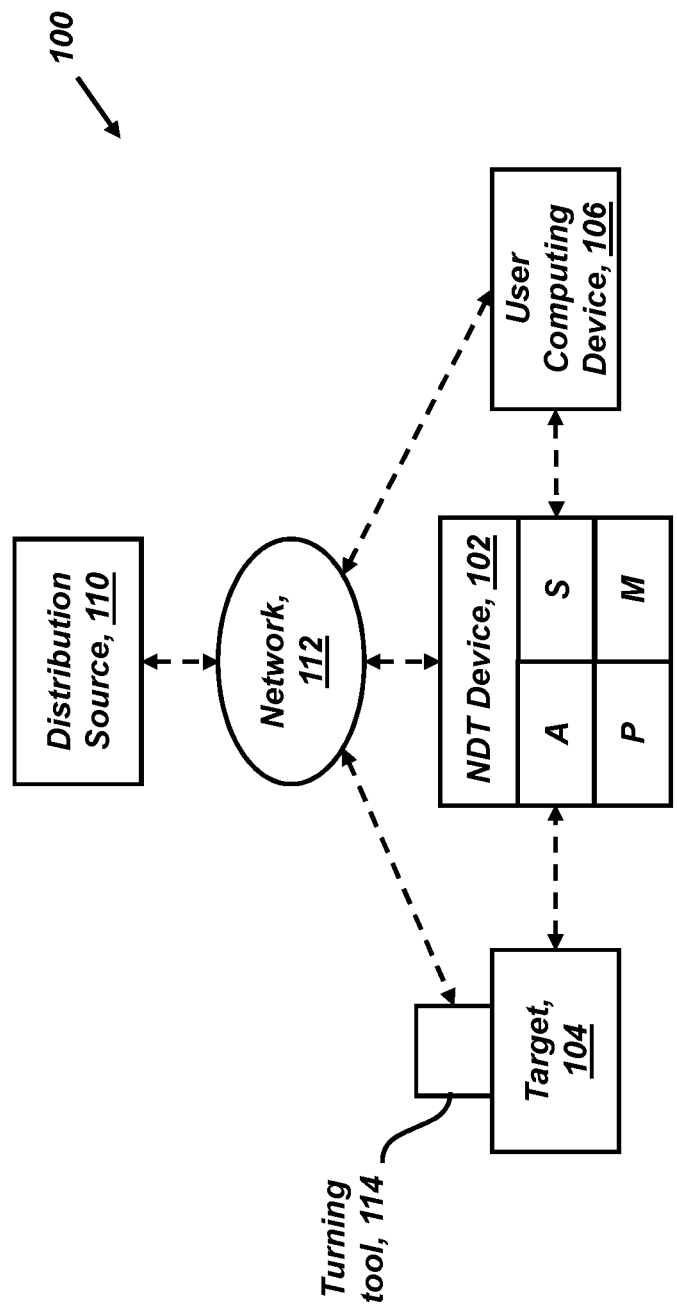
FIG. 1 is a diagram illustrating one exemplary embodiment of an operating environment including a customizable non-destructive testing (NDT) device.

FIG. 1 illustrates one exemplary embodiment of an operating environment 100 containing a customizable non-destructive testing (NDT) device 102 configured to perform non-destructive testing of a target 104. The NDT device 102 can be in communication with a user computing device 106 and a distribution source 110, either directly or via a network 112. Examples of the target 104 can include, but are not limited to, turbomachinery, equipment, pipes, conduits, underwater locations, curves, bends, inside or outside of an aircraft system, and the like. As shown, the NDT device 102 can include an articulation system A, one or more sensors S, one or more processors P, and one or more memory M.

The NDT device 102 can be any device suitable for visible or non-visible non-destructive testing. Examples of NDT devices 102 for visible NDT inspection can include borescopes and cameras (e.g., pan-zoom-tilt (PZT) cameras), and corresponding illumination devices. Examples of NDT devices 102 for non-visual NDT inspection can include x-ray devices, eddy current devices, and ultrasonic devices. Accordingly, the one or more sensors S can be any sensor(s) suitable for emitting and/or sensing signals (e.g., electromagnetic radiation (e.g., visible light, x-rays), ultrasound, etc.) It can be appreciated that this list of the NDT devices 102 is not exhaustive and other types of NDT devices can be employed without limit.

The user computing device 106 can be a desktop or mobile computing device. Examples of mobile computing devices can include tablets, cellular phones (e.g., smart phones), laptops, and the like. The user computing device 106 can be communicatively coupled to the NDT device 102 via a wired or wireless communication, either directly or via the network 112. Beneficially, communication between the user computing device 106 and the NDT device 102 via the network 112 can facilitate operation of the NDT device 102 from any geographic location, including geographic locations remote from the physical location about to undergo inspection.

In operation, the processor P of the NDT device 102 can execute one or more applications stored within the memory M to implement NDT functions, including but not limited to manipulation of the NDT device 102, NDT acquisition by one or more of the sensors S, analysis employing NDT data obtained by the NDT data acquisition, or NDT output (e.g., storage and/or display) acquired NDT data and/or analysis.

As discussed in greater detail below, tools (e.g., software development kits (SDKs), application programming interfaces (APIs), and other toolkits for development of the customized NDT-specific applications can be provided by the manufacturer of the NDT device 102 for development of customized NDT-specific applications by customers or third parties. The customized NDT-specific applications can have programmatic access to one or more functions of the NDT device 102 and provide additional NDT functions, different than those provided by stock applications. Customizable NDT functions can include, but are not limited to, NDT manipulation, NDT configuration, NDT data acquisition, analysis of data acquired by the one or more sensors S, or output of acquired NDT data and analyses employing the acquired NDT data. The customized NDT-specific applications can further modify and/or replace one or more graphical user interfaces generated by the stock applications. In this manner, the manner in which NDT inspection is performed (e.g., user interaction with the NDT device 102, acquisition of NDT data, analysis of data) and NDT output can be customized to a customer's needs. Such customization can simplify NDT evaluation, minimize human error, and reduce the time required for NDT evaluation, improving outcomes and providing cost savings.

To facilitate distribution, customized NDT-specific applications can be further stored by one or more distribution sources 110. The distribution sources 110 can be accessed via private networks or public networks, as necessary. Such networks can be hosted by any one of the NDT device 102 manufacture, NDT device 102 customers, and third parties. As discussed in greater detail below, distribution via public networks can be employed to facilitate wide-scale distribution, while private networks can be employed to limit distribution of customized NDT-specific applications to authorized parties.

Customized configuration of an NDT inspection by customized NDT-specific applications can include input of one or more parameters employed by the sensors S during NDT inspection. As an example, when the NDT device 102 is employed for visual inspection, the configuration parameters can be camera settings, level of external illumination, patterns of external illumination, etc. Similarly, when the NDT device 102 is employed for non-visual inspection, the configuration parameters can be those appropriate for the non-visual sensor S (e.g., x-ray devices, eddy current devices, and ultrasonic devices). Furthermore, when one or more of the sensors S are digital devices, NDT configuration can include file parameters, such as file format, quality, file naming conventions, file size, file output location, and the like.

Customized manipulation by customized NDT-specific applications can include movement of the NDT device 102 with respect to the target 104, movement of the target 104 with respect to the NDT device 102, and combinations thereof. As discussed in greater detail below, one or more movements of the NDT device 102 with respect to the target 104 can be controlled by a motor. Such motor-controlled movements can be controlled by the customized NDT-specific applications.

In further embodiments, movement of the target 104 with respect to the NDT device can be performed by a turning tool 114 coupled to the target 104. The turning tool 114 can be in communication with the NDT device 102 and/or the user computing device 106 via the network 112. During NDT inspection, the customized NDT-specific applications can be employed to command the turning tool 114 to move the target 104 to specific locations. In certain embodiments, movements of the target 104 and NDT device 102 can be partially or completely automated, which can shorten the time required to perform inspection.

Customized NDT acquisition can include acquisition of any data by the sensors. Examples can include capture of pictures, capture of video, and measurements.

Customized NDT output by the customized NDT-specific applications can include selection and output of any information generated during NDT inspection, as well as a location for such output. Examples of generated information include one or more of the acquired NDT data itself, results of any analysis performed using the acquired NDT data, and capture (e.g., keylogging) of any input provided to devices executing the customized NDT-specific applications (e.g., the NDT device 102 and/or user computing device 106). Such input can include keylogging, user notes, and the like.

In further embodiments, one or more graphical user interfaces generated by the stock applications can be modified and/or replaced by the customized NDT-specific applications. Examples can include, but are not limited to, soft keys for control of the NDT device 102, pop-up windows, menu options, and the like.

Figure 2:
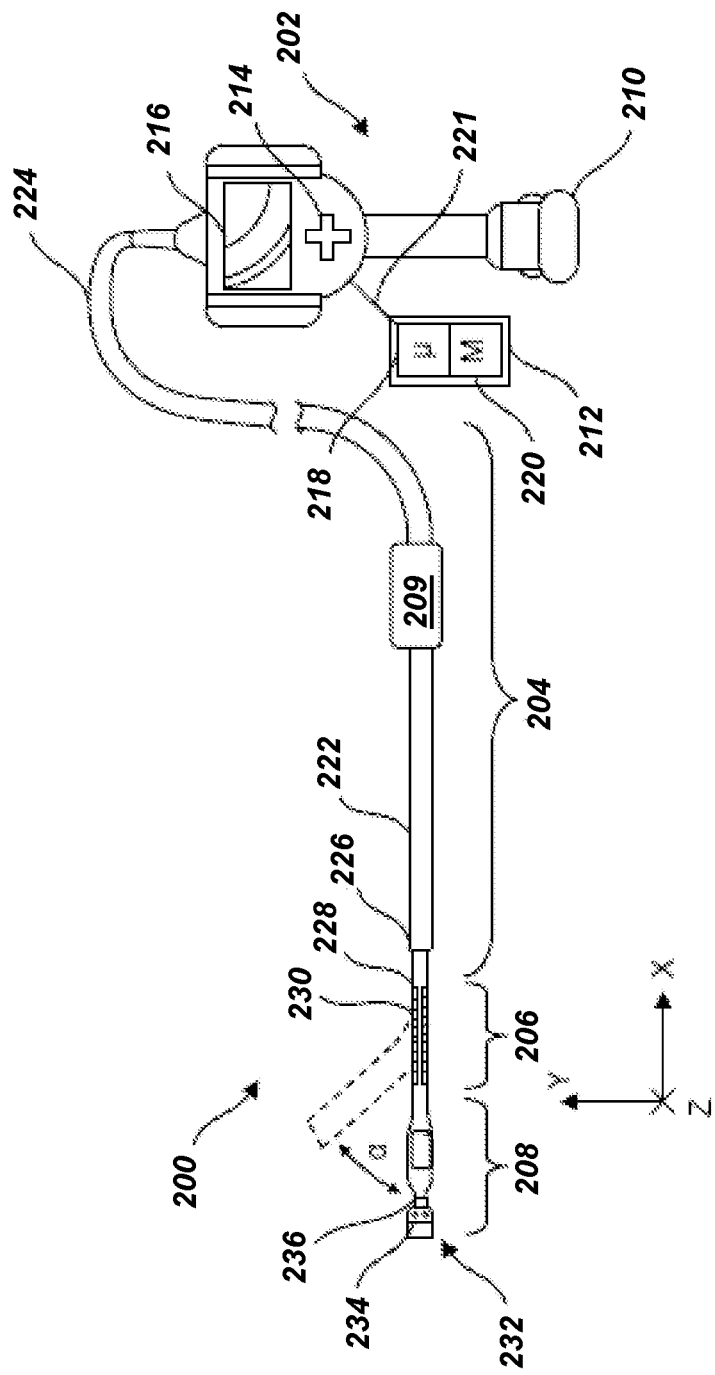
FIG. 2 is a diagram illustrating one exemplary embodiment of a customizable NDT device in the form of a borescope.

FIG. 2 is a diagram illustrating one exemplary embodiment of the NDT device 102 in the form of a borescope 200. The borescope 200 includes a control unit 202, a conduit section 204, a bendable articulation section 206, and a head section 208.

In one embodiment, the sections 204, 206, 208 can have different lengths and can be integral with one another, or can be detachable from one another, depending on specific applications. For example, to lengthen the conduit section 204, the shorter conduit section 204 can be removed and a longer conduit section 204 can be attached to the control unit 202. As depicted, the conduit section 204 is suitable for insertion into a variety of different targets 104, such as inside turbomachinery, equipment, pipes, conduits, underwater locations, curves, bends, inside or outside of an aircraft system, and the like.

In an alternative embodiment, the borescope 200 can include a probe driver 209 coupled to the conduit section 204. The probe driver 209 can include a motor (not shown) configured to translate and/or rotate one or more of the sections 204, 206, 208 to facilitate insertion of the probe head 208 into the target 104.

The control unit 202 can include a control unit housing 210, a controller 212, a directional input 214, and a screen 216. The controller 212 can include a processor 218 and a readable memory 220 containing computer readable instructions which can be executed by the processor 218 in order to actuate the borescope 200.

The controller 212 can be communicatively coupled to the control unit 202 via one or more signals 221. The controller 212 can also be arranged within the control unit housing 210, or can be arranged outside the control unit housing 210. The directional input 214 can be configured for receipt of user input (e.g., direction controls) to the control unit 202 for actuation of the borescope 200. The screen 216 can display visual information being received by an optical sensor arranged in the head section 208, which can allow the user to better guide the borescope 200 using the directional input 214. The directional input 214 and the screen 216 can be communicatively coupled to the controller 212 via the one or more signals 121, which can be a hard-wired connection or a wireless signal, such as WI-FI™ or Bluetooth™.

The conduit section 204 can include a tubular housing 222 including a proximal end 224 and a distal end 226. The tubular housing 222 can be a flexible member along its whole length, or can be rigid at the proximal end 224 and become more flexible travelling down the length of the conduit section 204 towards the distal end 226. In certain embodiments, the tubular housing 222 can be formed from a non-porous material to prevent contaminants from entering the borescope 200 via the conduit section 204.

The control unit 202 can be arranged at the proximal end 224 of the tubular housing 222, and the bendable articulation section 206 can be arranged at the distal end of the tubular housing 222. The bendable articulation section 206 can include a bendable neck 228 and washers 230. The bendable neck 228 can be arranged at the distal end 226 of the tubular housing 122, and is able to be actuated 360° in the Y-Z plane. In an embodiment, the washers 230 can be wobble washers, which allow the washers 230 to slide against one another as the bendable neck 228 is articulated, keeping the shape of the bendable articulation section 206. The washers 230 can be copper or some other suitable rigid material, and have angled surfaces which allow for the bendable neck 228 to be articulated. The bendable neck 228 can be wrapped in a non-porous material to prevent contaminants from entering the borescope 200 via the bendable articulation section 206 (e.g., between the washers 230 during articulation of the bendable neck 228.

The head section 208 can include a head assembly 232. The head assembly 232 can include one or more lights 234 (e.g., LEDs or a fiber optic bundle with lights at the proximal end), a camera 236, and one or more sensors 238 that are configured to collect data about the surrounding environment (e.g., lights 234, a camera 236, etc.)

The camera 236 of the borescope 200 can provide images and video suitable for inspection to the screen 216 of the control unit 202. The lights 234 can be used to provide for illumination when the head section 208 is disposed in locations having low light or no light. The sensor 238 can record data including temperature data, distance data, clearance data (e.g., distance between a rotating element and a stationary element), flow data, and so on. In certain embodiments, the borescope 200 includes a plurality of replacement head assemblies 232. For example, the head assemblies 232 can include retrieval tips such as snares, magnetic tips, gripper tips, and the like. The head assemblies 232 can additionally include cleaning and obstruction removal tools, such as wire brushes, wire cutters, and the like. The head assemblies 232 can additionally include tips having differing optical characteristics, such as focal length, stereoscopic views, 3-dimensional (3D) phase views, shadow views, etc. Additionally or alternatively, the head section 208 can include a removable and replaceable portion of the head section 108. Accordingly, a plurality of the head sections 208, bendable necks 228, and conduit section 204 can be provided at a variety of diameters from approximately one millimeter to ten millimeters or more.

During use, the bendable articulation section 206 and the probe driver 209 can be controlled, for example, by the control inputs (e.g., relative control gestures, physical manipulation device) from the directional input 214. The directional input can be a joystick, D-pad, touch pad, trackball, optical sensor, or a touchscreen over the screen 216. The directional input 214 can also be a similar device that is located outside the control unit housing 210 and connected by wire or wireless means. In particular, a set of control inputs can be used to control the bendable articulation section 206 and/or the probe driver 209. The bendable articulation section 206 can steer or "bend" in various dimensions, while the conduit section 204 can translate and/or rotate, using any combination of actuators and wires arranged within the control unit 202, to adjust the orientation (e.g., a positioning) of the head section 208. The actuators can be electric, pneumatic, or ultrasonically operated motors or solenoids, shape alloy, electroactive polymers, dielectric elastomers, polymer muscle material, or other materials. For example, the bendable articulation section 206 and the probe driver 209 can enable movement of the head section 208 in an X-Y plane, X-Z plane, and/or Y-Z plane. Indeed, the directional input 214 can be used to perform control actions suitable for disposing the head section 208 at a variety of angles, such as the depicted angle α. In this manner, the head section 208 can be positioned to visually inspect desired locations.

Once the head section 208 is in a desired position, the camera 236 can operate to capture, for example, a stand-still visual image or a continuous visual image, which can be displayed on the screen 216 of the control unit 202, and can be recorded by the borescope 200. In embodiments, the screen 216 can be multi-touch touch screens using capacitance techniques, resistive techniques, infrared grid techniques, and the like, to detect the touch of a stylus and/or one or more human fingers. Additionally or alternatively, captured visual images can be transmitted into a separate storage device for later reference.

Prior to installation of one or more customized applications on the borescope 200 (e.g., the controller 212), the above-discussed functionality of the borescope 200 (e.g., NDT configuration, NDT manipulation, NDT acquisition, NDT analysis, and/or NDT output) can be implemented by execution of one or more stock applications by the borescope 200 stored in the memory 220 and executed by the processor 218. After installation of the one or more customized applications on the borescope 200, at least one of the stock functions can be modified and/or replaced for when the customized NDT-specific application(s) are executed.

The modified or replaced functions can facilitate NDT inspection. Given the wide variety of NDT devices, prospective targets, and possible analyses of data acquired during NDT inspection, it can be difficult for stock applications to cover every possible use case. Furthermore, customers can desire to maintain certain NDT testing procedures and/or analyses proprietary and private. Accordingly, the ability to customize functions of NDT devices 102, such as borescope 200, by use of customizable applications can significantly improve the ease of NDT inspection, increase throughput, and/or reduce NDT inspection cost.

A variety of different functionality of the NDT device 102 (e.g., borescope 200) can be customized in this manner. Examples can include, but are not limited to:

Execution of two-dimensional and three-dimensional NDT measurement acquisition and analysis routines (e.g., steering control [translation, rotation, bending of conduit head 208], triggering of measurements, interaction with turning tool(s)

Control of scene illumination (e.g., via the one or more lights 234).

Receipt of NDT specific control inputs (e.g., joystick, knobs, borescope tip IMU) from outside the NDT device 102 (e.g., user computing device 106).

Access to on-board computing resources (e.g., processor 218, memory 220) for machine vision purposes (e.g., DNN model training, inferencing, other NDT measurement transformation).

Modification of stock graphical user interfaces.

Addition of soft-keys for control of the NDT device 102 (e.g., articulation, illumination, NDT data acquisition).

Access to and display of NDT measurements and analyses.

Execution of proprietary software and display through stock graphical user interfaces.

Activation of customized functions by selection of a user interface object (e.g., a button) within an otherwise stock graphical user interface.

Display of one or more overlays upon live video.

Enabling network access:

For output of user inputs (e.g., touchscreen input, keystrokes) on the NDT device 102 to the user computing device 106 and/or other external computing devices.

For output of video to the user computing device 106 and/or other external computing devices.

Enabling access to file systems stored and managed by the NDT device 102.

The customized NDT-specific applications have been described above as being stored and executed on the NDT device 102. However, in alternative embodiments, the customized NDT-specific application can be stored and executed by the user computing device 106, alone or in combination with the NDT device 102. Thus, the user computing device 106 can be employed, alone or in combination with the NDT device 102 to control one or more of NDT configuration, NDT acquisition, NDT analysis, NDT output (e.g., transmission and/or display), and graphical user interfaces for the same.

Figure 3:
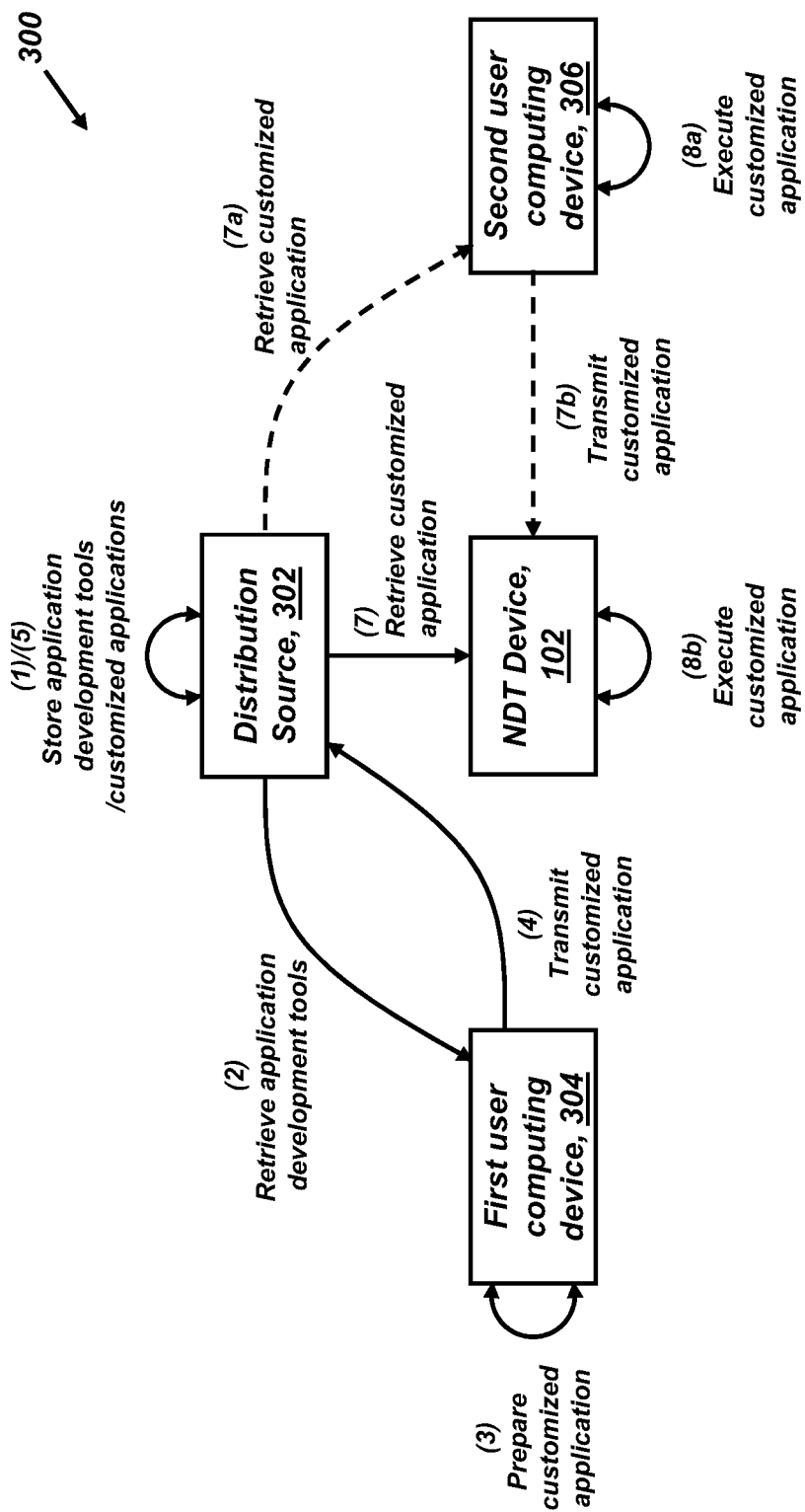
FIG. 3 is a block diagram illustrating information flow for distribution of customized applications for the NDT device of FIG. 1.

FIG. 3 is a block diagram illustrating one exemplary embodiment of an operating environment 300 configured to implement the customized NDT-specific applications. As shown, development tools for preparing the customized NDT-specific applications can be stored at a distribution source 302. The development tools can be prepared by the manufacturer of the NDT device 102. A first user computing device 304 can retrieve the development tools from the distribution source 302 and prepare a customized NDT-specific application. As an example, the first user computing device 304 can be operated by an NDT device 102 customer or third party. The prepared customized NDT-specific application can be further transmitted to the distribution source 302, or another network accessible computing device, for further distribution. As an example, in one embodiment, the customized NDT-specific application can be received by the NDT device 102 directly from the distribution source 302 or indirectly via a second user computing device 306 (e.g., the user computing device 106). Once retrieved by the second user computing device 306 and/or the NDT device 102, the customized NDT-specific application can be executed.

The distribution source 302 can be operated on a public or private basis. In one embodiment, a public distribution source can permit retrieval of the development tools and/or customized NDT-specific applications by any party, either without charge or in exchange for a fee, similar to a smartphone app store. As an example, it can be beneficial for a manufacturer of the NDT device 102 to operate the distribution source 302 on a public basis for retrieval of the development tools and/or customized applications in order to encourage sales and provide after sales support for the NDT device 102.

In another embodiment, a private distribution source can limit retrieval of the development tools and/or customized NDT-specific applications to only authorized parties, either without charge or in exchange for a fee. As an example, it can be beneficial for a customer that owns the NDT device 102 to operate the distribution source 302 on a private basis for retrieval of customized NDT-specific applications that employ proprietary knowledge (e.g., NDT measurement analyses) in order to keep such customized NDT-specific applications private.

Figure 4:
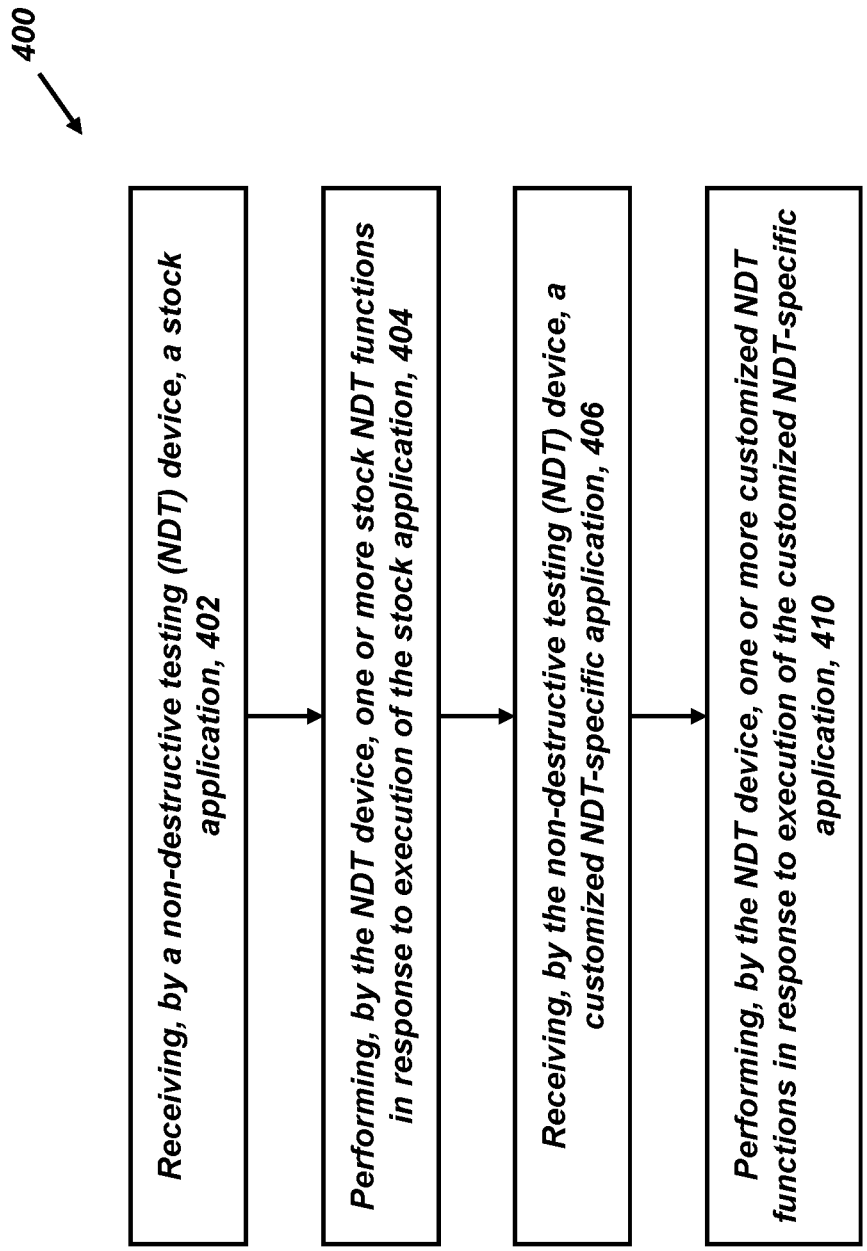
FIG. 4 is a flow diagram illustrating one exemplary embodiment of a method for customizing the functionality of NDT devices.

FIG. 4 is a flow diagram illustrating one embodiment of a method 400 for providing customized functionality for the NDT device 102 and is described with reference to FIGS. 1-2. As shown, the method 400 includes operations 402-410. However, in alternative embodiments, the method can include greater or fewer operations and the operations can be performed in an order different than that illustrated in FIG. 4.

In operation 402, the stock application is received by the NDT device 102. As an example, the stock application can be installed by a manufacturer of the NDT device 102.

In operation 404, the NDT device 102 can perform one or more stock NDT functions in response to execution of the stock application. The one or more stock NDT functions can include at least one of a first manipulation of the NDT device, a first NDT data acquisition by one of the sensors S of the NDT device 102, or first analysis employing data acquired by the first NDT acquisition, or a first NDT output.

In operation 406, the NDT device 102 can receive one or more customized NDT-specific applications after receipt of the one or more stock applications. As an example, the customized NDT-specific applications can be received directly from the distribution source 302 or indirectly via the user computing device 106.

In operation 410, the NDT device 102 can perform one or more custom NDT functions in response to execution of the customized NDT-specific application(s). The one or custom NDT functions can be different from the stock NDT functions and can include at least one of a second manipulation of the NDT device 102, a second NDT data acquisition by one of the sensors S of the NDT device, a second analysis employing data obtained by the second NDT data acquisition, or a second NDT output.

Exemplary technical effects of the methods, systems, and devices described herein include, by way of non-limiting example customization of NDT-specific functionality of NDT devices. In one aspect, customers and third parties can develop applications that implement proprietary NDT measurement processes, analyses, and/or displays. The functionality provided by such applications can be integrated with existing "stock" applications to a desired degree, from simple combination of stock and customized features to entire replacement of the stock features with customized features. In another further aspect, such applications can be easily distributed through one or more centralized data sources (e.g., application stores). Such distribution can be kept private, allowing the applications to remain proprietary to the developing party, or public, allowing wider release to any interested party. Furthermore, applications originally developed internally by a given party can be subsequently resold to a broader audience.

Certain exemplary embodiments have been described to provide an overall understanding of the principles of the structure, function, manufacture, and use of the systems, devices, and methods disclosed herein. One or more examples of these embodiments have been illustrated in the accompanying drawings. Those skilled in the art will understand that the systems, devices, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, in the present disclosure, like-named components of the embodiments generally have similar features, and thus within a particular embodiment each feature of each like-named component is not necessarily fully elaborated upon.

The subject matter described herein can be implemented in analog electronic circuitry, digital electronic circuitry, and/or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine-readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processor of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, (e.g., EPROM, EEPROM, and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having a display device, e.g., a CRT (cathode ray tube) or LCD (liquid crystal display) monitor, for displaying information to the user and a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The techniques described herein can be implemented using one or more modules. As used herein, the term "module" refers to computing software, firmware, hardware, and/or various combinations thereof. At a minimum, however, modules are not to be interpreted as software that is not implemented on hardware, firmware, or recorded on a non-transitory processor readable recordable storage medium (i.e., modules are not software per se). Indeed "module" is to be interpreted to always include at least some physical, non-transitory hardware such as a part of a processor or computer. Two different modules can share the same physical hardware (e.g., two different modules can use the same processor and network interface). The modules described herein can be combined, integrated, separated, and/or duplicated to support various applications. Also, a function described herein as being performed at a particular module can be performed at one or more other modules and/or by one or more other devices instead of or in addition to the function performed at the particular module. Further, the modules can be implemented across multiple devices and/or other components local or remote to one another. Additionally, the modules can be moved from one device and added to another device, and/or can be included in both devices.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and front-end components. The components of the system can be interconnected by any form or medium of digital data communication, e.g., a communication network. Examples of communication networks include a local area network ("LAN") and a wide area network ("WAN"), e.g., the Internet.

Approximating language, as used herein throughout the specification and claims, may be applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

One skilled in the art will appreciate further features and advantages of the invention based on the above-described embodiments. Accordingly, the present application is not to be limited by what has been particularly shown and described, except as indicated by the appended claims. All publications and references cited herein are expressly incorporated by reference in their entirety.

The invention claimed is:

1. A method for customizing non-destructive testing, comprising:
    receiving, by a non-destructive testing (NDT) device, a stock application;
    performing, by the NDT device, one or more stock NDT functions of the stock application, the one or more stock NDT functions comprising at least one of a first manipulation of the NDT device, a first NDT data acquisition by a sensor of the NDT device, a first analysis employing data obtained by the first NDT data acquisition, or a first NDT output;
    receiving, by the NDT device, one or more custom NDT-specific applications, wherein the one or more custom NDT-specific applications are different from the stock application;
    performing, by the NDT device, one or more custom NDT functions of the one or more custom NDT-specific applications, the one or more custom NDT functions being different from stock NDT functions and comprising at least one of a second manipulation of the NDT device, a second NDT data acquisition by a sensor of the NDT device, a second analysis of the first NDT, or a second NDT output.

2. The method of claim 1, wherein the NDT device is a borescope.

3. The method of claim 2, wherein the first and second manipulations are different articulations of a tip of the borescope.

4. The method of claim 2, wherein the second manipulation is at least one of a translation or rotation of a probe driver of the borescope.

5. The method of claim 1, wherein the one or more custom NDT functions includes input of one or more configuration settings of the sensor that performs the second NDT data acquisition.

6. The method of claim 1, wherein the second manipulation is movement of the target with respect to the NDT device performed by a turning tool coupled to the target.

7. The method of claim 1, wherein the custom NDT functions further comprise control of an illumination of the target.

8. A non-transitory computer-readable medium comprising instructions configured to:
receive one or more stock applications by an NDT device;
performing, by the NDT device, one or more stock NDT functions of the stock application response to execution of the stock application, the one or more stock NDT functions including comprising at least one of a first manipulation of the NDT device, a first NDT data acquisition by a sensor of the NDT device, a first analysis employing data acquired by the first NDT data acquisition, or a first NDT output;
receive one or more custom NDT-specific applications by the NDT device, wherein the one or more custom NDT-specific applications are different from the stock application;
performing, by the NDT device, one or more custom NDT functions of the one or more custom NDT-specific applications, the one or more custom NDT functions being different from the stock NDT functions and comprising at least one of a second manipulation of the NDT device, a second NDT data acquisition by a sensor of the NDT device, a second analysis employing data obtained by the second NDT data acquisition, or a second NDT output.

9. The non-transitory computer-readable medium of claim 8, wherein the NDT device is a borescope.

10. The non-transitory computer-readable medium of claim 9, wherein the first and second manipulation are different articulations of a tip of the borescope.

11. The non-transitory computer-readable medium of claim 9, wherein the second manipulation is at least one of a translation or rotation of a probe driver of the borescope.

12. The non-transitory computer-readable medium of claim 8, wherein the one or more custom NDT functions includes input of one or more configuration settings of the sensor that performs the second NDT data acquisition.

13. The non-transitory computer-readable medium of claim 8, wherein the second manipulation is movement of the target with respect to the NDT device performed by a turning tool coupled to the target.

14. The non-transitory computer-readable medium of claim 8, wherein the custom NDT functions further comprise control of an illumination of the target.

15. The method of claim 1, wherein the one or more custom NDT-specific applications are received from a distribution source either directly or via a network.

16. The non-transitory computer-readable medium of claim 8, wherein the one or more custom NDT-specific applications are received from a distribution source either directly or via a network.

* * * * *